United States Patent
Besselink et al.

(10) Patent No.: US 6,428,634 B1
(45) Date of Patent: Aug. 6, 2002

(54) NI-TI-NB ALLOY PROCESSING METHOD AND ARTICLES FORMED FROM THE ALLOY

(75) Inventors: Petrus A. Besselink, Enschede (NL); Rohit C. L. Sachdeva, Plano, TX (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 08/839,965

(22) Filed: Apr. 24, 1997

Related U.S. Application Data

(63) Continuation of application No. 08/221,638, filed on Mar. 31, 1994, now abandoned.

(51) Int. Cl.$^7$ .......................... C22C 14/00; C22C 19/00
(52) U.S. Cl. ................. 148/421; 148/402; 148/426; 420/417; 420/441; 420/902
(58) Field of Search ............... 148/402, 421, 148/426; 420/902, 441, 417

(56) References Cited

U.S. PATENT DOCUMENTS

| | | | |
|---|---|---|---|
| 4,304,613 A | 12/1981 | Wang | 148/402 |
| 4,502,896 A | 3/1985 | Duerig | 148/402 |
| 4,533,411 A | 8/1985 | Melton | 148/402 |
| 4,631,094 A | 12/1986 | Simpson | 148/402 |
| 4,654,092 A | 3/1987 | Melton | 148/402 |
| 4,770,725 A | 9/1988 | Simpson | 148/402 |
| 4,849,032 A | * 7/1989 | Kawaguchi | 148/402 |
| 5,358,796 A | * 10/1994 | Nakamura et al. | 428/660 |

FOREIGN PATENT DOCUMENTS

| | | | |
|---|---|---|---|
| EP | 0143580 | 6/1985 | |
| EP | 0161066 | 11/1985 | |
| EP | 0185452 | 6/1986 | |
| JP | 58157934 | 9/1983 | |
| JP | 62-37353 | * 2/1987 | ................. 148/402 |
| JP | 63096234 | 4/1988 | |

OTHER PUBLICATIONS

Min Piao et al., "Characteristics of Deformation and Transformation in $Ti_{44}Ni_{47}Nb_9$ Shape Memory Alloy," Material Transactions, JIM, vol. 33, No. 4 (1992) pp. 346–353.
D. E. Hodgson et al., "Shape Memory Alloys", Metals Handbook/vol. 2, Ed. 10, (1990) pp. 897–902.
L. C. Zhao et al., "Transformation and Mechanical Behavior of a $Ni_{47}Ti_{44}Nb_9$ Shape Memory Alloy", MRS Int'l. Mtg. on Adv. Mats. vol. 9 (1989) pp. 171–176.
Min Piao et al., *Effects of Nb Addition on the Microstructure of Ti–Ni Alloys*, Materials Transactions, JIM, vol. 33, No. 4 (1992) pp. 337–345.
R. Sachdeva et al., *Shape Memory NiTi Alloys–Applications in Dentistry*, Materials Science Forum vols. 56–58 (1990) pp. 693–698.

* cited by examiner

*Primary Examiner*—John Sheehan
(74) *Attorney, Agent, or Firm*—Wood, Herron & Evans, LLP

(57) ABSTRACT

A method of processing a Ni—Ti—Nb based alloy which contains from about 4 to about 14 atomic percent Nb and in which the ratio of atomic percent Ni to atomic percent Ti is from about 3.8 to 1.2, comprising working the alloy sufficient to impart a textured structure to the alloy, at a temperature below the recrystallisation temperature of the alloy. Preferably, the alloy is worked at least 10%, by a technique such as rolling or drawing, or another technique which produces a similar crystal structure. The alloy has increased stiffness compared with Ni—Ti binary alloys with superelastic properties.

4 Claims, 2 Drawing Sheets

NI-TI-NB ALLOY PROCESSING METHOD AND ARTICLES FORMED FROM THE ALLOY

This application is a continuation of application Ser. No. 08/221,638, filed Mar. 31, 1994, abandoned.

BACKGROUND TO THE INVENTION

This invention relates to a method for processing a Ni—Ti—Nb based alloy, to such alloys per se, and to articles made from such alloys.

Ni—Ti based alloys are known to exhibit shape memory properties, associated with transformations between martensite and austenite phases. These properties include thermally induced changes in configuration in which an article is first deformed from a heat-stable configuration to a heat-unstable configuration. Subsequent exposure to increased temperature results in a change in configuration from the heat-unstable configuration towards the original heat-stable configuration.

They also exhibit enhanced elastic properties compared with materials which do not exhibit martensite-austenite transformations. The superelastic transformation of a shape memory alloy is discussed in "Engineering Aspects of Shape Memory Alloys", T W Duerig et al, on page 370, Butterworth-Heinemann (1990. Subject matter disclosed in that document is incorporated in this specification by this reference to the document. The transformation is depicted in FIG. 1 of the accompanying drawings. FIG. 2 shows how stress varies with strain during a reversible elastic deformation. It will be seen that, as strain increases, stress increases initially approximately linearly. This behavior is reversible, and corresponds to conventional elastic deformation. Subsequent increases in strain are accompanied by little or no increase in stress, over a limited range of strain to the end of the "loading plateau". The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point (which is characteristic of the superelastic behaviour with which the present invention is concerned) along which stress changes little with reducing strain. At the end of the unloading plateau, stress reduces with reducing strain. The unloading plateau stress is also defined by the inflection point on the stress/strain graph. Any residual strain after unloading to zero stress is the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys", on page 376. Typical values for commercially available Ni—Ti binary alloys are:

Loading plateau stress 500 MPa

Unloading plateau stress 150–280 MPa

Permanent set (after 6% deformation) <0.5%

Plateau length 6%–8%

Elastic modulus 40–50 GPa

The thermally induced recovery shape memory properties of Ni—Ti—Nb based alloys have been investigated. It has been found that the characteristic temperatures of the shape transformation of certain Ni—Ti—Nb based alloys can be modified by appropriate treatment, so that alloys which would normally exist in the austenite phase at ambient temperature can be stored in the martensite phase at room temperature in the deformed configuration from which they will recover when heated. Such alloys are disclosed in EP-A-185452.

The advantageous properties of the Ni—Ti—Nb based alloys disclosed in EP-A-185452 lie in their ability to respond to a treatment to change temporarily the characteristic temperatures of the thermally induced change in configuration. No consideration has been given to their superelastic properties.

Indeed, the fact that the transformation hysteresis can be expanded in the way referred to above (to make an alloy stable temporarily at ambient temperature in the martensite phase) suggests that the alloys would not be useful as superelastic alloys, it is established that it is preferable in a superelastic alloy for hysteresis to be as small as possible (see for example "Engineering Aspects of Shape Memory Alloys", T W Duerig et al, page 382, Butterworth-Heinemann (1990)).

SUMMARY OF THE INVENTION

The present invention is concerned with the previously unrecognised superelastic behaviour of Ni—Ti—Nb alloys, having properties which are superior to those of other alloys which exhibit superelastic behaviour, such as Ni—Ti binary alloys.

The invention provides a method of processing a Ni—Ti—Nb based alloy which comprises working an article formed from such an alloy at a temperature which is less than the recrystallisation temperature of the alloy. Recrystallisation of an alloy involves the formation of new, defect-free, low energy grains or crystals, which consume and replace highly worked, high energy grains. It involves the loss of a textured structure introduced by working.

Accordingly, in one aspect, the invention provides a method of processing a Ni—Ti—Nb based alloy which contains from about 4 to about 14 atomic percent Nb and in which the ratio of atomic percent Ni to atomic percent Ti is from about 0.8 to 1.2, comprising subjecting the alloy to at least about 10% work by a technique which comprises at least one of rolling and drawing, and operations which produce a similar textured crystal structure in the alloy, at a temperature below the recrystallisation temperature of the alloy.

The method of the invention gives rise to beneficial properties in the processed alloy. In particular, the plateau stresses on both loading and unloading are increased significantly compared with conventional binary alloys. Furthermore, the permanent set for a given deformation can in some circumstances be reduced compared with such conventional alloys. These benefits are important. They make it possible for articles to be made which can store relatively larger amounts of elastic energy per unit volume of material. As a corollary, they make it possible to keep small the size of components made using the article. The increased stiffness that is apparent in articles made using the treated alloy is an attractive feature when the articles are used in, for example, eyeglass frames, orthodontic archwires and guidewires for catheters. The method of the invention provides this increased stiffness without an undesirable permanent set, which has accompanied previous attempts to increase stiffness in superelastic shape memory alloy materials, for example by varying the compositions of the alloys.

A further advantage of the alloys of the invention is that the tendency found in some Ni—Ti based alloys to revert to an R-phase (a transitional phase between the austenite and martensite phases) is reduced. This reduces the tendency of elastic modulus to be lowered. It is important for certain applications, for example when the alloy is used in a catheter guidewire when the modulus controls the geometric stability of the wire against lateral stresses.

Yet another advantage of the invention is that it provides articles with superelastic properties which are more resistant to corrosion than articles formed from alloys used previously for their superelastic properties. An advantage arising from the corrosion resistance is the compatibility of the materials which makes them suitable for use in medical applications.

Accordingly, the invention provides a Ni—Ti—Nb based alloy whose superelastic properties are such that (a) the loading plateau on loading at 25° C. is at least about 600 MPa, preferably at least about 700 MPa, more preferably at least about 800 MPa, for example at least about 900 MPa, and (b) the permanent set after tensile deformation at 25° C. to 6% is less than about 2.5%, preferably less than about 1.5%, more preferably less than about 1.0%.

Preferably, the work is imparted to the alloy by a technique which comprises at least one of rolling and drawing, and similar operations which produce a textured crystal structure. Surprisingly, it has been found that the beneficial properties which result from the method of the invention arise from working by these techniques. By working the alloy using rolling or drawing (including die-less drawing) or a similar techniques, it has been found to be possible to produce an alloy which displays good ductility and good strength. Other working techniques can produce alloys with one of these properties, but not both.

Particularly preferred working techniques include rod and wire drawing.

Figure 1:
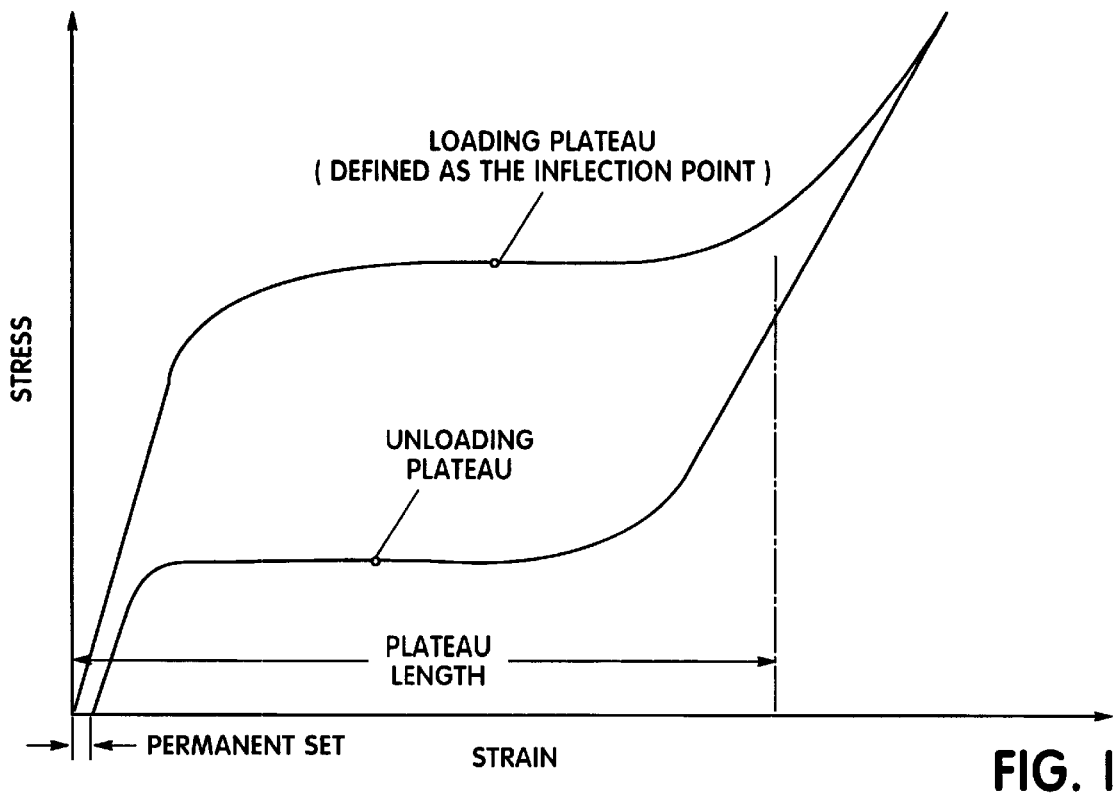
FIG. 1 is a stress-strain diagram depicting how stress varies with strain during a reversible elastic deformation.

With respect to the objection to the application because of alterations which have not been initialed and/or dated, a properly executed Declaration in compliance with 37 C.F.R. §1.67(a) is being prepared and will be submitted in follow-up to this response.

The alloy on which the method is practised comprises nickel, titanium and niobium. It is preferred that the alloy contains at least about 4 at. % niobium, especially at least about 6 at. %, for example about 9 at. %. It is preferred that the alloy contains not more than about 14 at. % niobium, more preferably not more than about 12 at. %, especially not more than about 10 at. %.

It is preferred that the ratio of atomic percent Ni to atomic percent Ti is at least about 0.8, more preferably at least about 0.9. It is preferred that the said ration is not more than about 1.2, preferably not more than about 1.1.

The alloy can contain a quantity of an element other than nickel, titanium and niobium. Examples of suitable additional elements include Fe, Co, Cr, V and Al. When an additional element is included, it can be appropriate to adjust the ratio of nickel to titanium to maintain the characteristic transformation temperatures of the alloy (especially the $A_0$ temperature) at appropriate levels.

The method of the invention can comprise subjecting the article made from the alloy to work under warm work conditions, that is at a temperature that is less than the recrystallisation temperature, but more than the temperature at which recovery processes take place. Preferred conditions for such working might be, for example at a temperature which is more than about 300° C., more preferably more than about 400° C., especially more than about 450° C. The warm work will preferably be conducted at a temperature not more than about 700° C., more preferably not more than about 625° C., especially not more than about 500° C.

The method of the invention can comprise subjecting the article made from the alloy to work under cold work conditions, that is at a temperature which is less than that at which a significant level of recovery processes take place. Preferred conditions for such working might be, for example at a temperature which is more than about –100° C., more preferably more than about –50° C., especially more than about 10° C. The cold work will preferably be conducted at a temperature not more than about 200° C., more preferably not more than about 100° C., especially not more than about 50° C.

The alloy can be annealed before it is worked.

The method of the invention can include a step in which the alloy is heat treated after it has been worked. When it is heat treated in this way, the work that is to be measured in the context of the method of the invention is the work that is imparted after the heat treatment. It is particularly preferred that the method includes a subsequent heat treatment step when the alloy is cold worked. The heat treatment is preferably carried out at a temperature which is less than the recrystallisation temperature of the alloy. For example, the heat treatment might be carried out at a temperature not more than about 700° C., preferably less than about 625° C., more preferably less than about 500° C. The heat treatment is preferably carried out at a temperature which is more than about 300° C., more preferably more than about 400° C. The period for which the heat treatment is conducted will depend on the temperature that is chosen.

Preferably the amount of work imparted to the article will be at least 10%, more preferably at least 12%, especially at least about 15%, for example at least about 20%. The work can be measured as a change in cross-sectional area of the article.

Preferably, the cross-sectional area of the article after the working step of the method will be not more than about 5 mm$^3$, more preferably not more than about 3.5 mm$^3$, especially not more than about 2.5 mm$^3$.

The method of the invention can include steps in addition to the working and optional heat treatment steps referred to above, including for example bending, swaging, pressing and so on. Any such additional steps will generally be carried out after the working and heat treatment steps.

The article of the invention can have configurations for a number of different applications. For example, it might be in the form of a wire or a tube. The article might be used in eyeglass frames. The article is suitable for use in medical (including dental) applications, for example as an orthodontic wire, an orthodontic coil spring, an endosseous dental implant, endodontic reamers and files and other instruments used in dentistry, a catheter, a catheter guidewire, flexible cutting tools for arthroscopic procedures or tissue excision and other instruments used in surgery (such as a reamer or file), vascular clips, vascular, billiary and urological stents, bone anchor pins, and as components (such as a spring) of any of these articles. The article can also be used in a suture needle or a surgical needle.

Accordingly, in another aspect, the invention provides an article which comprises a component formed from a Ni—Ti—Nb based alloy, the component exhibiting superelastic properties. The article can be used in, for example, any of the applications referred to above.

EXAMPLE

A Ni—Ti—Nb wire with a circular cross-section and an initial diameter of 0.54 mm, and a composition of 46 at. % Ni, 65 at. % Ti and 9% Nb, was heat treated at 600° C. and drawn to a diameter of 0.45 mm (leaving 33% cold work in the material). After drawing at room temperature, the wire was heat treated at 400° C. for 10 minutes. Room temperature tensile testing gave the following properties:

Loading plateau stress 900 MPa

Unloading plateau stress 500 MPa

Permanent set (after 6% deformation) 0.3%

Plateau length 8.5%

Young's modulus 65 GPa

Figure 2:
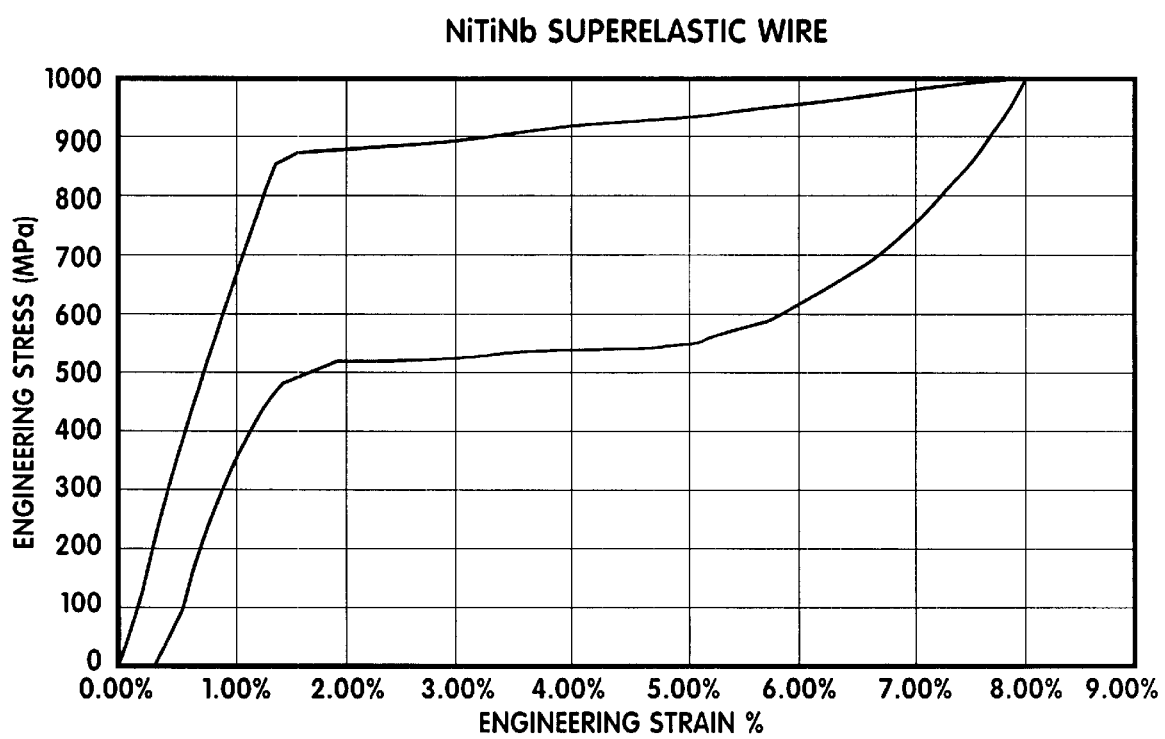
FIG. 2 is a stress-strain diagram for an orthodontic archwire made of an alloy in accordance with the present invention.
Figure 3:
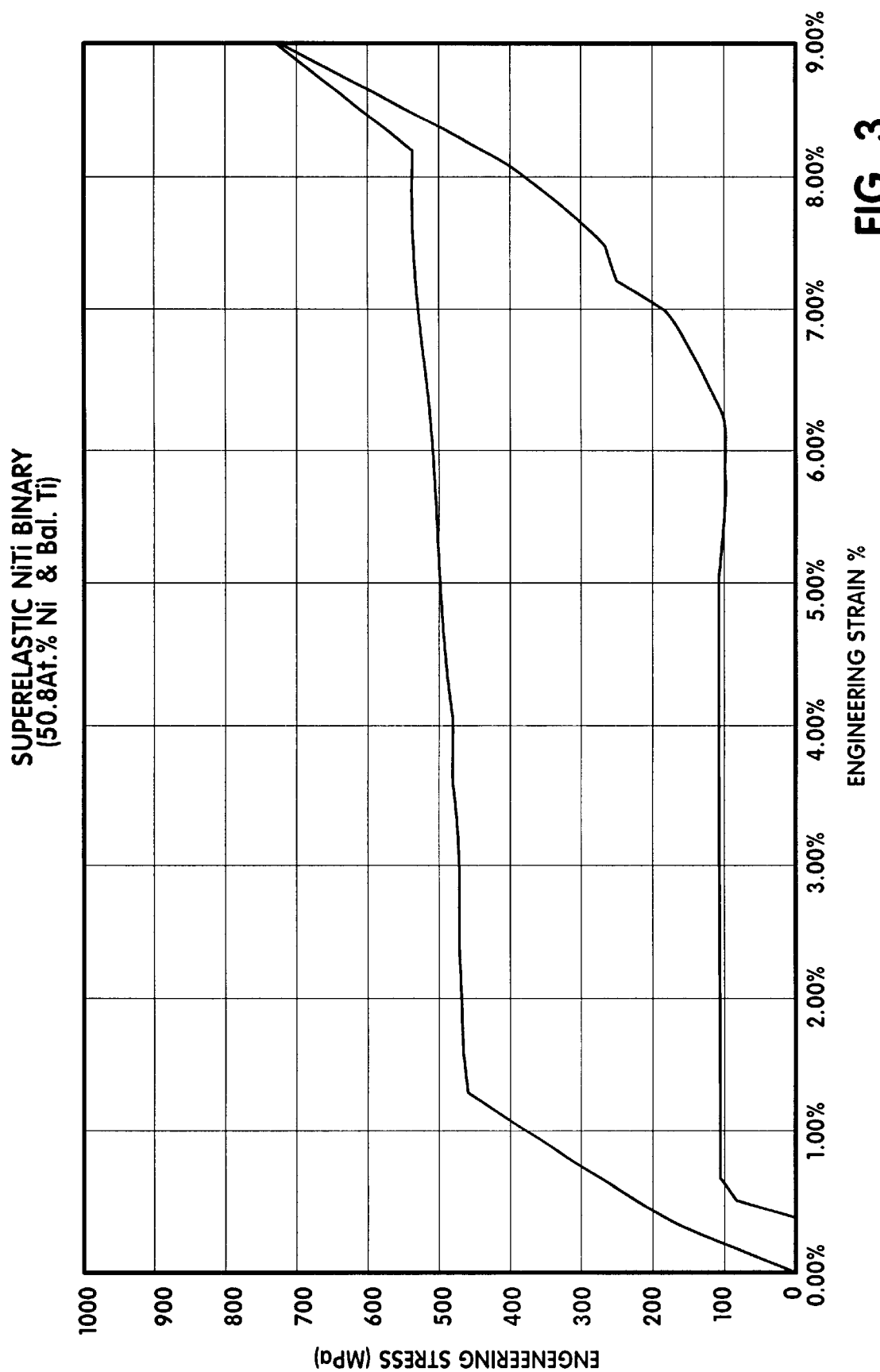
FIG. 3 is a stress-strain diagram for a typical Ni—Ti orthodontic archwire.

FIG. 2 shows the properties of the resulting wire compared to typical archwire available on the market shown in FIG. 3.

The invention is disclosed in this specification with reference to specific features. It will be apparent that modifications can be made to the invention as disclosed. Accordingly, the scope of the protection is to be defined by the claims.

What is claimed is:

1. An article made from a Ni—Ti—Nb based alloy, said article selected from the group consisting of a component of an eyeglass frame, an orthodontic wire, a catheter, a catheter guidewire, an instrument for use in dentistry, and an instrument for use in surgery;

said Ni—Ti—Nb alloy exhibiting superelastic properties, including a loading plateau stress on loading at 25° C. of at least about 600 MPa, and comprising about 9% atomic Nb, and wherein the ratio of atomic % Ni to atomic % Ti is in the range of about 0.8 to 1.2.

2. An article made from a Ni—Ti—Nb based alloy, said article selected from the group consisting of a component of an eyeglass frame, an orthodontic wire, a catheter, a catheter guidewire, a bone anchor pin, an endosseous dental implant, a vascular clip, a vascular stent, a billiary stent, a urological stent, an endodontic reamer, and an endodontic file;

said Ni—Ti—Nb alloy exhibiting superelastic properties, including a loading plateau stress on loading at 25° C. of at least about 600 MPa, and comprising about 9% atomic Nb, and wherein the ratio of atomic % Ni to atomic % Ti is in the range of about 0.8 to 1.2.

3. An article according to claim 1, said alloy having a loading plateau stress of about 900 MPa.

4. An article according to claim 3, said alloy having an unloading plateau stress of about 500 MPa.

* * * * *

UNITED STATES PATENT AND TRADEMARK OFFICE
CERTIFICATE OF CORRECTION

PATENT NO.  : 6,428,634 B1
DATED       : August 6, 2002
INVENTOR(S) : Petrus A. Besselink et al.

It is certified that error appears in the above-identified patent and that said Letters Patent is hereby corrected as shown below:

<u>Title page,</u>
Item [57], ABSTRACT,
Line 4, "3.8" should be -- 0.8 --.

<u>Column 1,</u>
Line 30, "FIG. 2" should be -- FIG. 1 --.

<u>Column 2,</u>
Line 15, "alloys," should be -- alloys; --.

<u>Column 3,</u>
Lines 44-48, should be deleted.

<u>Column 4,</u>
Line 46, "$mm^3$," should be -- $mm^2$, --.
Line 46, "3.5 $mm^3$," should be -- 3.5 $mm^2$, --.
Line 47, "2.5 $mm^3$." should be -- 2.5 $mm^2$. --.

Signed and Sealed this

Twenty-eighth Day of January, 2003

JAMES E. ROGAN
*Director of the United States Patent and Trademark Office*